United States Patent
Greenleaf et al.

(10) Patent No.: US 8,659,975 B2
(45) Date of Patent: Feb. 25, 2014

(54) VIBRATION GENERATION AND DETECTION IN SHEAR WAVE DISPERSION ULTRASOUND VIBROMETRY WITH LARGE BACKGROUND MOTIONS

(75) Inventors: James F. Greenleaf, Rochester, MN (US); Shigao Chen, Rochester, MN (US); Yi Zheng, Cold Spring, MN (US); Aiping Yao, St. Cloud, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 595 days.

(21) Appl. No.: 12/992,228

(22) PCT Filed: May 15, 2009

(86) PCT No.: PCT/US2009/044163
§ 371 (c)(1),
(2), (4) Date: Nov. 11, 2010

(87) PCT Pub. No.: WO2009/140607
PCT Pub. Date: Nov. 19, 2009

(65) Prior Publication Data
US 2011/0063950 A1    Mar. 17, 2011

Related U.S. Application Data

(60) Provisional application No. 61/053,264, filed on May 15, 2008.

(51) Int. Cl.
*G01S 15/00*    (2006.01)
(52) U.S. Cl.
USPC .................... 367/99; 367/87; 367/89; 367/93

(58) Field of Classification Search
USPC .................... 367/141–190, 87–116
See application file for complete search history.

(56) References Cited

U.S. PATENT DOCUMENTS

| | | | |
|---|---|---|---|
| 3,023,609 | A | 3/1962 | Schubring |
| 4,061,017 | A | 12/1977 | Sloane et al. |

(Continued)

FOREIGN PATENT DOCUMENTS

| | | | | |
|---|---|---|---|---|
| TR | WO00/10638 | * | 3/2000 | |
| WO | 00/10638 A2 | | 3/2000 | |

OTHER PUBLICATIONS

Chen, et al., Complex Stiffness Quantification Using Ultrasound Stimulated Vibrometry, 2003 IEEE Ultrasonics Symposium, pp. 941-944.

(Continued)

*Primary Examiner* — Luke Ratcliffe
(74) *Attorney, Agent, or Firm* — Quarles & Brady, LLP (57) ABSTRACT

A method for measuring a mechanical property of a subject includes using an ultrasonic transducer to apply ultrasonic vibration pulses to a vibration origin in the subject in an on-off time sequence in order to impart a harmonic motion at a prescribed frequency to the subject, and when the vibration pulses are off, preferably using the same transducer to apply ultrasonic detection pulses to a motion detection point and to receive echo signals therefrom in order to sense the harmonic motion on the subject at the motion detection point The ultrasonic detection pulses are interspersed with the vibration pulses and can be applied in a non-uniform manner From the received ultrasonic echo signals, a harmonic signal is detected and a characteristic such as amplitude or phase of the detected harmonic signal is calculated using a Kalman filter or interpolation.

15 Claims, 7 Drawing Sheets

(56) References Cited

U.S. PATENT DOCUMENTS

| | | | |
|---|---|---|---|
| 4,947,851 | A | 8/1990 | Sarvazyan et al. |
| 5,086,775 | A | 2/1992 | Parker et al. |
| 5,487,306 | A | 1/1996 | Fortes |
| 5,505,090 | A | 4/1996 | Webster |
| 5,606,971 | A | 3/1997 | Sarvazyan |
| 5,672,830 | A | 9/1997 | Rogers et al. |
| 5,810,731 | A | 9/1998 | Sarvazyan et al. |
| 5,903,516 | A | 5/1999 | Greenleaf et al. |
| 5,921,928 | A | 7/1999 | Greenleaf et al. |
| 5,974,881 | A | 11/1999 | Donskoy et al. |
| 5,974,889 | A | 11/1999 | Trantow |
| 5,991,239 | A | 11/1999 | Fatemi-Booshehri et al. |
| 5,995,620 | A * | 11/1999 | Wigren .................. 379/406.09 |
| 6,045,504 | A | 4/2000 | Muzilla et al. |
| 6,068,597 | A | 5/2000 | Lin |
| 6,245,016 | B1 | 6/2001 | Daft et al. |
| 6,711,954 | B2 | 3/2004 | Drake, Jr. |
| 6,715,354 | B2 | 4/2004 | Wooh |
| 6,764,448 | B2 | 7/2004 | Trahey et al. |
| 6,899,680 | B2 | 5/2005 | Hoff et al. |
| 6,951,544 | B2 | 10/2005 | Trahey et al. |
| 6,984,209 | B2 | 1/2006 | Hynynen et al. |
| 7,753,847 | B2 | 7/2010 | Greenleaf et al. |
| 7,785,259 | B2 | 8/2010 | Zheng et al. |
| 2002/0007118 | A1 | 1/2002 | Adachi et al. |
| 2002/0095087 | A1 | 7/2002 | Mourad et al. |
| 2004/0167403 | A1 | 8/2004 | Nightingale et al. |
| 2004/0260180 | A1 | 12/2004 | Kanai et al. |
| 2005/0075565 | A1 | 4/2005 | Satoh |
| 2005/0119568 | A1 | 6/2005 | Salcudean et al. |
| 2005/0165306 | A1 | 7/2005 | Zheng et al. |
| 2005/0167596 | A1 | 8/2005 | Rothenfusser et al. |
| 2005/0252295 | A1 | 11/2005 | Fink et al. |
| 2006/0000281 | A1 | 1/2006 | Harris |
| 2006/0036174 | A1 * | 2/2006 | Guracar et al. ................ 600/458 |
| 2006/0169029 | A1 | 8/2006 | Heyman |
| 2007/0038095 | A1 * | 2/2007 | Greenleaf et al. ............. 600/438 |
| 2008/0302187 | A1 | 12/2008 | Huber et al. |
| 2010/0010346 | A1 | 1/2010 | Greenleaf et al. |

OTHER PUBLICATIONS

Michishita, et al., Ultrasonic Measurement of Minute Displacement of Object Cyclically Actuated by Acoustic Radiation Force, Jpn. J. Appl. Phys., 2003, 42:4608-4612.

Nightingale, et al., On the Feasibility of Remote Palpation Using Acoustic Radiation Force, J. Acoust. Soc. Am., 2001, 110(1):625-634.

Ruvolo, et al., Skin Viscoelasticity Displays Site-and Age-Dependent Angular Anisotropy, Skin Pharmacol. Physiol., 2007, 20:313-321.

Vexler, et al., Evaluation of Skin Viscoelasticity and Anisotropy by Measurement of Speed of Shear Wave Propagation with Viscoelasticity Skin Analyzer, J. Invest Dermatol., 1999, 113:732-739.

Zhang, et al., Excitation and Measurement of Flexural Waves in Arterial Vessels, 2003 IEEE Ultrasonics Symposium, pp. 1883-1886.

PCT International Search Report and Written Opinion, PCT/US05/45964, Jun. 21, 2006.

United States Patent and Trademark Office, Office Action Summary and Detailed Action, U.S. Appl. No. 11/536,330, filed Nov. 29, 2007.

Amendment (Response to Nov. 29, 2007 Office Action), U.S. Appl. No. 11/536,330, filed Feb. 29, 2008.

United States Patent and Trademark Office, Office Action Summary and Detailed Action, U.S. Appl. No. 11/536,330, filed Aug. 18, 2008.

Amendment (Response to Aug. 18, 2008 Office Action), U.S. Appl. No. 11/536,330, filed Nov. 18, 2008.

United States Patent and Trademark Office, Office Action Summary and Detailed Action, U.S. Appl. No. 11/536,330, filed Feb. 6, 2009.

Appellant's Brief on Appeal, U.S. Appl. No. 11/536,330, filed Jun. 8, 2009.

United States Patent and Trademark Office, Office Action Summary and Detailed Action, U.S. Appl. No. 11/536,330, filed Oct. 8, 2009.

Amendment (Response to Oct. 8, 2009 Office Action), U.S. Appl. No. 11/536,330, filed Jan. 8, 2010.

United States Patent and Trademark Office, Notice of Allowance, U.S. Appl. No. 11/536,330, filed May 7, 2010.

International Search Report under date of mailing of Jul. 17, 2009 corresponding to PCT/US2009/044163.

* cited by examiner

VIBRATION GENERATION AND DETECTION IN SHEAR WAVE DISPERSION ULTRASOUND VIBROMETRY WITH LARGE BACKGROUND MOTIONS

CROSS-REFERENCE TO RELATED APPLICATIONS

This application claims the benefit of, and incorporates by reference herein by its entirety, PCT International Patent Application PCT/US2009/044163 filed on May 15, 2009 and U.S. Provisional patent application Ser. No. 61/053,264 filed on May 15, 2008, and entitled "Vibration Generation and Detection in Shearwave Dispersion Ultrasound Vibrometry With Large Background Motions".

STATEMENT REGARDING FEDERALLY SPONSORED RESEARCH

This invention was made with government support under EB002167 awarded by the National Institute of Biomedical Imaging and Bioengineering. The government has certain rights in the invention.

BACKGROUND OF THE INVENTION

The field of the invention is coherent imaging using vibratory energy, such as ultrasound and, in particular, systems and methods for shearwave dispersion ultrasound vibrometry ("SDUV").

There are a number of modes in which ultrasound can be used to produce images of objects. The ultrasound transmitter may be placed on one side of the object and the sound transmitted through the object to the ultrasound receiver placed on the other side. With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction," "backscatter," or "echo" mode).

There are a number of well known backscatter methods for acquiring ultrasound data. In the so-called "A-scan" method, an ultrasound pulse is directed into the object by an ultrasound transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and their amplitude is used to modulate the brightness of pixels on a display. The location of the transducer and the time delay of the received echo signals locates the pixels to be illuminated. With the B-scan method, enough data are acquired from which a two-dimensional image of the refractors can be reconstructed. Rather than physically moving the transducer over the subject to perform a scan it is more common to employ an array of transducer elements and electronically move an ultrasonic beam over a region in the subject.

The transducer typically has a number of piezoelectric elements arranged in an array and driven with separate voltages ("apodizing"). By controlling the time delay (or phase) and amplitude of the applied voltages, the ultrasonic waves produced by the piezoelectric elements ("transmission mode") combine to produce a net ultrasonic wave focused at a selected point. By controlling the time delay and amplitude of the applied voltages, this focal point can be moved in a plane to scan the subject.

The same principles apply when the transducer is employed to receive the reflected sound ("receiver mode"). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the echo signal received by each transducer array element.

There are a number of electronic methods for performing a scan using a transducer having an array of separately operable elements. These methods include linear array systems and phased array systems.

A linear array system includes a transducer having a large number of elements disposed in a line. A small group of elements are energized to produce an ultrasonic beam that travels away from the transducer, perpendicular to its surface. The group of energized elements is translated along the length of the transducer during the scan to produce a corresponding series of beams that produce echo signals from a two-dimensional region in the subject. To focus each beam that is produced, the pulsing of the inner elements in each energized group is delayed with respect to the pulsing of the outer elements. The time delays determine the depth of focus which can be changed during scanning. The same delay factors are applied when receiving the echo signals to provide dynamic focusing during the receive mode.

The second common form of ultrasonic imaging is referred to as phased array sector scanning ("PASS"). Such a scan is comprised of a series of measurements in which all of the elements of a transducer array are used to transmit a steered ultrasonic beam. The system then switches to receive mode after a short time interval, and the reflected ultrasonic wave is received by all of the transducer elements. Typically, the transmission and reception are steered in the same direction, $\theta$, during each measurement to acquire data from a series of points along a scan line. The receiver is dynamically focused at a succession of ranges, R, along the scan line as the reflected ultrasonic waves are received. A series of measurements are made at successive steering angles, $\theta$, to scan a pie-shaped sector of the subject. The time required to conduct the entire scan is a function of the time required to make each measurement and the number of measurements required to cover the entire region of interest at the desired resolution and signal-to-noise ratio. For example, a total of 128 scan lines may be acquired over a sector spanning 90 degrees, with each scan line being steered in increments of 0.70 degrees.

The same scanning methods may be used to acquire a three-dimensional image of the subject. The transducer in such case is a two-dimensional array of elements which steer a beam throughout a volume of interest or linearly scan a plurality of adjacent two-dimensional slices.

Recently, an ultrasound technique for measuring mechanical properties of tissues called shearwave dispersion ultrasound vibrometry ("SDUV") was developed and described, for example, in pending U.S. patent application Ser. Nos. 10/956,464 and 11/536,330, which are herein incorporated by reference in their entirety. A focused ultrasound beam, operating within FDA safety limits, is applied to a subject to generate harmonic shear waves in a tissue of interest. The propagation speed of the induced shear wave is frequency dependent, or "dispersive," and relates to the mechanical properties of the tissue of interest. Shear wave speeds at a number of frequencies are measured by pulse echo ultrasound and subsequently fit with a theoretical dispersion model to inversely solve for tissue elasticity and viscosity. These shear wave speeds are estimated from the phase of tissue vibration that is detected between two or more points with known distance along the shear wave propagation path.

One feature of the SDUV method is the use of a so-called "binary pushing pulse" that allows the operation of one single array ultrasound transducer for both motion excitation and the echo signal detection. The transducer focuses ultrasound at one location, the "vibration origin," to vibrate the tissue of interest and then electronically steers its focus to another location, a "motion detection point," for echo signal vibration detection. Instead of continuously vibrating the tissue of interest, the "pushing" ultrasound is turned on during a vibration time period to vibrate the tissue and turned off to provide a time window for the pulse echo motion detection. When the pushing pulse is off, a series of short ultrasound pulses is transmitted to the motion detection location and a corresponding series of echo signals is received and processed to determine the tissue vibration. This intermittent pulse sequencing strategy allows both the production of a shear wave and the monitoring of its propagation at the same time with a single array transducer.

A technical challenge for the SDUV method, however, is that the shear wave generated by the pushing ultrasound is small and difficult to detect with pulse echo ultrasound. A Kalman filtering process is often applied to the vibration time-sequence, which is demodulated from the series of ultrasound echoes received from the same motion detection point, to reliably extract the phase of tissue vibration. However, when performing SDUV in vivo, gross tissue motion due to, for example, respiratory and cardiac activity is large and confounds the estimation of phases. With larger shear wave magnitudes the effects of this background motion can potentially be mitigated. Larger shear waves can be produced in the subject by increasing the intensity of the pushing pulse; however, current ultrasound scanners may not be able to provide an ultrasound beam intensity high enough to meet the requirement of this solution. In addition, the intensity of diagnostic ultrasound is limited by the FDA, typically rendering an increase in pushing pulse intensity unfeasible.

It would therefore be desirable to provide a method for shearwave dispersion ultrasound vibrometry ("SDUV") that compensates for large background motions.

SUMMARY OF THE INVENTION

The present invention overcomes the aforementioned drawbacks by providing a method for shearwave dispersion ultrasound vibrometry ("SDUV") that compensates for large background motions. In particular, harmonic shear wave motion with a greater magnitude is produced through the application of an ultrasonic vibration pulse having a long duration. The ultrasonic vibration pulse is applied during an "on" time period having a duration, $\Delta T$. The longer duration vibration pulse is accompanied by a series of ultrasonic detection pulses having an increased pulse repetition frequency ("PRF") and correspondingly decreased pulse repetition period ("PRP"). Kalman filtering is applied to the echo signals received from the motion detection point to detect a signal indicative of the imparted harmonic shear wave motion. The Kalman filter specifically accounts for the non-uniform temporal sampling resulting from the "on" time period duration being larger than the PRP of the detection pulses; that is, $\Delta T > PRP$.

It is an aspect of the invention to provide a method for simultaneously determining shear wave speeds for multiple harmonic motion frequencies. This is achieved by modifying the measurement vector employed during the Kalman filtering process to account for the multiple frequency components of the harmonic motion. This provides a method for Kalman filtering that does not first require applying a band-pass filter to the echo signals. In turn, this allows for the application of the non-uniform temporal pattern where $\Delta T > PRP$. In general, the multiple frequency Kalman filter adaptation decreases errors that arise during the estimation of the phase and amplitude of the harmonic motion by properly accounting for higher harmonics in that motion.

It is another aspect of the invention to provide a method for compensating for large background motions in SDUV by modeling the background motion as a random process during Kalman filtering. This is achieved by adding additional state variables to the state equation employed during the Kalman filtering process. Exemplary additional state variables include the displacement and velocity of the background tissue motion. The transition matrix in the state equation is correspondingly modified to account for these additional variables, as is the measurement vector. By modeling the background tissue motion during the Kalman filtering process, SDUV methods are more applicable to in vivo applications, in which physiological motion arising from cardiac and respiratory activity can confound the detection of the relatively small shear wave motion.

It is yet another aspect of the invention to provide a method for applying detection ultrasound pulses to two locations in an interleaved manner. Echoes from each location will have different time delays and the Kalman filter can be modified to accommodate this delay in time for proper phase estimation.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

In shearwave dispersion ultrasound vibrometry methods ("SDUV"), where a tissue of interest is buried deeply beneath other tissues, optical methods for measuring the very small harmonic motions of the subject tissue cannot be used. This problem is solved by employing an ultrasonic imaging system that interrogates the tissue of interest with a pulsed ultrasound beam and examines the resulting echo signals to measure the phase and amplitude of the harmonic motion imparted to the subject tissue. The challenge is to extract this information from the echo signals where the amplitude of the harmonic motion is at the submicron level. Moreover, it is challenging to extract this information where the harmonic motion exists in the presence of larger gross tissue motion resulting from, for example, cardiac and respiratory activity. To compensate for large background tissue motion, two general adaptations are provided. First, a pushing pulse with a longer duration is applied to induce shear waves of larger intensity, making them easier to differentiate from background motion. Second, the background motion can be compensated through modeled, thereby reducing its influence on the estimated phase and amplitude of the desired harmonic shear wave motion.

General Description

In general, the displacement of a point in a tissue that is in harmonic motion can be represented in the following form:

$$D(t)=D_0 \sin(\omega_s t+\phi_s) \qquad \text{Eqn. (1);}$$

where $D_0$ is an amplitude of the motion displacement, $\omega_s$ is the tissue vibration frequency, and $\phi_s$ is the tissue vibration phase. The velocity of this motion is then of the form:

$$v(t) = \frac{dD(t)}{dt} = v_0 \cos(\omega_s t + \phi_s); \qquad \text{Eqn. (2)}$$

where $v_0=D_0 \omega_s$ is an amplitude of the motion velocity. When a pulse echo ultrasound system is focused on the tissue motion, the motion is represented as oscillatory Doppler shifts in the received echo signals. The received echo signals, therefore, have the form:

$$r(t_f,t_s)=A(t_f,t_s)\cos(\omega_f t_f+\phi_f+\beta \sin(\omega_s t_s+\phi_s)) \qquad \text{Eqn. (3);}$$

where $A(t_f,t_s)$ is the amplitude of the complex envelope of the received echo signal; $t_f$ is fast time, which is representative of depth; $t_s$ is slow time, which is representative of pulse repetition; $\omega_f$ is the transmission center frequency; $\omega_s$ is again the tissue vibration frequency; $\phi_s$ is again the tissue vibration phase; and $\theta$ is an angle between the ultrasound beam and direction of tissue motion. The vibration becomes a phase term of the angular modulation. Furthermore, the modulation index, $\beta$, is:

$$\beta = \frac{2v_0 \omega_f \cos(\theta)}{\omega_s c}; \qquad \text{Eqn. (4)}$$

where c is the sound speed in the tissue. Quadrature demodulation of the received echo signals yields in-phase, $I(t_f,t_s)$, and quadrature, $Q(t_f,t_s)$, terms, which have the form:

$$I(t_f,t_s)=A(t_f,t_s)\cos(\beta \sin(\omega_s t_s+\phi_s)+\phi_f+\phi_0) \qquad \text{Eqn. (5);}$$

and $$Q(t_f,t_s)=A(t_f,t_s)\sin(\beta \sin(\omega_s t_s+\phi_s)+\phi_f+\phi_0) \qquad \text{Eqn. (6);}$$

respectively. Here, $\phi_0$ is a constant phase added during the quadrature demodulation to keep $I(t_f,t_s)$ nonzero; that is, to be either all positive, or all negative, in slow time at a location. In the end, this constant phase term is removed, as shown below. The arctangent of the ratio between $Q(t_f,t_s)$ and $I(t_f,t_s)$ is calculated accordingly:

$$s(t_f, t_s) = -\tan^{-1}\left(\frac{Q(t_f, t_s)}{I(t_f, t_s)}\right); \qquad \text{Eqn. (7)}$$

and $$y(t_s)=s(t_f,t_s)-\bar{s}(t_f,t_s)=\beta \sin(\omega_s t_s+\phi_s) \qquad \text{Eqn. (8);}$$

where $\bar{s}(t_f,t_s)$ is a mean value of $s(t_f,t_s)$ in slow time. If the sampling frequency in fast time is high, $I(t_f,t_s)$ and $Q(t_f,t_s)$ can be averaged with a limited length in fast time to reduce noise before $s(t_f,t_s)$ is calculated. A band-pass filter ("BPF") centered at the vibration frequency can improve $y(t_s)$ by reducing noise and distortions. The amplitude, $\beta$, of the oscillatory Doppler shifts can be directly estimated from $y(t_s)$ by:

$$\beta=\sqrt{2}\sigma_y \qquad \text{Eqn. (9);}$$

where $\sigma_y$ is a standard deviation of $y(t_s)$. However, the phase and amplitude of the Doppler shifts in Eqn. (8) can also be directly obtained by another quadrature demodulation, at the vibration frequency, in the direction of the slow time, which yields:

$$I(t_s)=\beta \cos(\phi_s) \qquad \text{Eqn. (10);}$$

and $$Q(t_s)=\beta \sin(\phi_s) \qquad \text{Eqn. (11).}$$

As a result of this demodulation, the amplitude can be obtained by:

$$\beta(t_s)=\sqrt{I(t_s)^2+Q(t_s)^2} \qquad \text{Eqn. (12);}$$

and the phase by:

$$\phi_s(t_s) = \tan^{-1}\left(\frac{Q(t_s)}{I(t_s)}\right). \qquad \text{Eqn. (13)}$$

The amplitude of the oscillatory Doppler shifts can also be directly measured by applying a turbulence estimation method to the received echo signals, $r(t_f,t_s)$, to estimate the variance of motion velocity.

In practice, the data acquired with the ultrasound system is noisy and stochastic in nature. Therefore, a Kalman filter process is employed to recursively estimate the phase and amplitude of the harmonic shear wave motion. As described, for example, by R. G. Brown and P. Y. C. Hwang in *Introduction To Random Signals and Applied Kalman Filtering*, 3rd Edition, John Wily & Sons, 1997, a Kalman filter is a numerical method used to track a time-varying signal in the presence of noise. If the signal can be characterized by some number of parameters that vary slowly with time, then Kalman filtering can be used to tell how incoming raw measurements should be processed to best estimate those parameters as a function of time. In this application, a Kalman filter extracts information about the imparted harmonic motion from random and noisy measurement data with known vibration frequency and unknown vibration amplitude and phase.

Figure 1A:
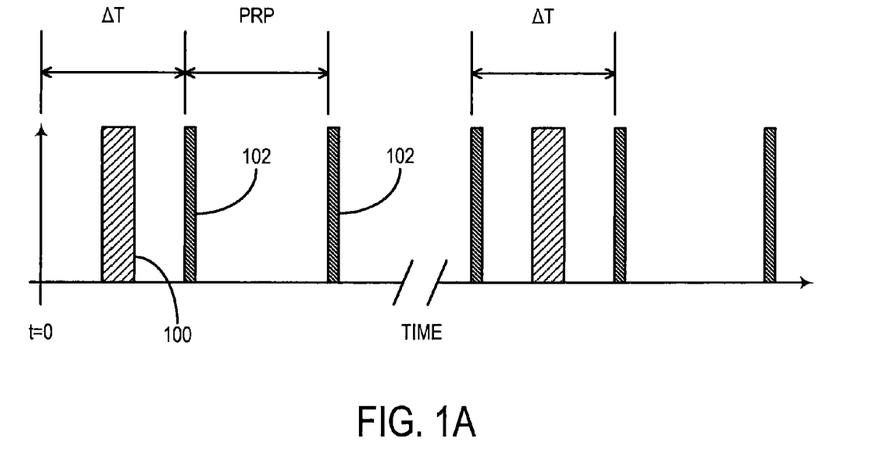
FIG. 1A is a pulse timing diagram indicating the application of ultrasonic vibration and detection pulses in a substantially uniform pattern.
Figure 2:
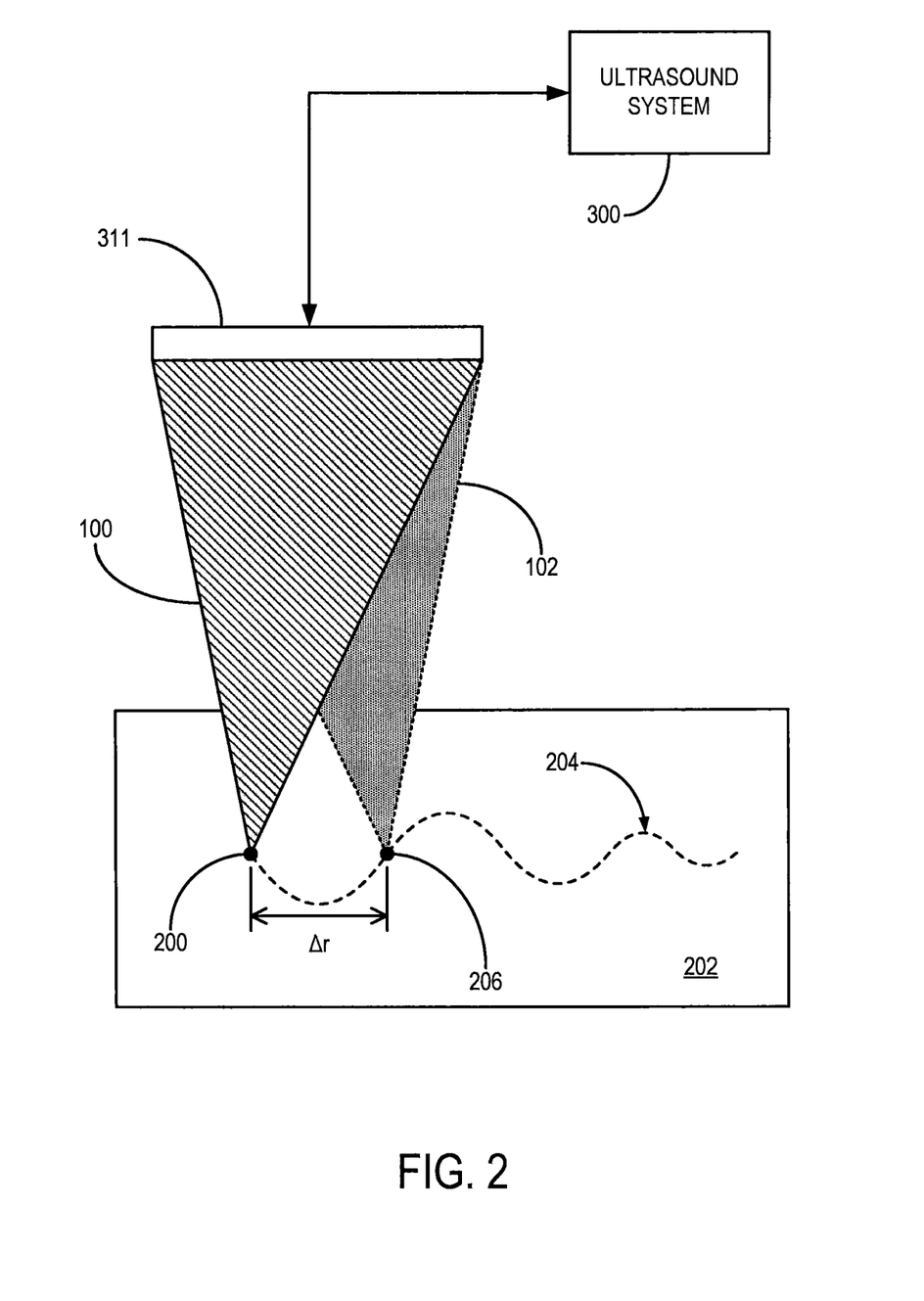
FIG. 2 is a block diagram of a vibroacoustography system that employs the present invention.

By way of example, and referring particularly now to FIGS. 1A and 2, an ultrasonic vibration pulse 100, or "pushing pulse," is applied to a vibration origin 200 in a tissue of interest 202 in order to induce harmonic shear wave motion 204 in the tissue 202. This shear wave motion 204 at a location in the tissue is interrogated by applying a series of ultrasonic detection pulses 102 to a motion detection point 206. Tissue vibration obtained from the $k^{th}$ ultrasound echo has the form:

$$y_k = [\sin(\omega_s kT) \quad \cos(\omega_s kT)] \begin{bmatrix} \beta\cos(\phi_s) \\ \beta\sin(\phi_s) \end{bmatrix} + n_k; \qquad \text{Eqn. (14)}$$

where $\omega_s$ is the frequency of the tissue vibration; T is the pulse repetition period ("PRP"), which is equal to the inverse of the pulse repetition frequency ("PRF"), or 1/PRF; $\beta$ and $\phi_s$ are the vibration amplitude and phase to be estimated, respectively; and $n_k$ is a white noise sequence having a variance, R. Eqn. (14) can be rewritten as:

$$y_k = H_k x_k + n_k \qquad \text{Eqn. (15);}$$

where $H_k$ is a measurement vector having the form:

$$H_k = [\sin(\omega_s kT) \cos(\omega_s kT)] \qquad \text{Eqn. (16);}$$

and $x_k$ is a state variable having the form:

$$x_k = \begin{bmatrix} \beta\cos(\phi_s) \\ \beta\sin(\phi_s) \end{bmatrix}; \qquad \text{Eqn. (17)}$$

In this form, the corresponding state equation is:

$$x_k = \Phi x_{k-1} + w_k \qquad \text{Eqn. (18);}$$

where $w_k$ is a white driving sequence vector that allows some variations in the vibration amplitude and phase, and $\Phi$ is a transition matrix, which has the form:

$$\Phi = \begin{bmatrix} 1 & 0 \\ 0 & 1 \end{bmatrix}. \qquad \text{Eqn. (19)}$$

When the ultrasonic detection pulses are transmitted at a fixed time interval T, as shown in FIG. 1A, Eqns. (15)-(18) are updated every T seconds in the Kalman filter. As is described, for example, in co-pending U.S. patent application Ser. No. 11/536,330, the Kalman filter is recursively applied to extract, from the noisy echo signals, the amplitude and phase of the underlying signal indicative of the harmonic shear wave motion. In such a manner, the amplitude and phase parameters have the form:

$$\beta = \sqrt{x_k[1]^2 + x_k[2]^2}; \qquad \text{Eqn. (20)}$$

$$\phi_s = a\tan^{-1}\left(\frac{x_k[2]}{x_k[1]}\right); \qquad \text{Eqn. (21)}$$

where $x_{k[1]} = \beta \cos(\phi_s)$ and $x_{k[2]} = \beta \sin(\phi_s)$, as illustrated in Eqn. (17). The above method can be applied to estimate the phase, $\phi_s$, of tissue vibration propagating over a known distance, $\Delta r$. As a result, the shear wave speed can be estimated using the phase change, $\Delta\phi_s$, that occurs over the distance, $\Delta r$, by:

$$c_s = \frac{\omega_s \Delta r}{\Delta \phi_s}; \qquad \text{Eqn. (22)}$$

which is further used to characterize elasticity and viscosity of the tissues, as will be described below.

In order to increase the magnitude of the shear wave induced in a tissue of interest, the pushing pulse duration is increased while maintaining its intensity. This provides an increase in the induced shear wave magnitude while maintaining ultrasound beam intensities within safe limits. When the duration of the pushing pulse is increased, however, a lower pulse repetition frequency ("PRF") is required to maintain a uniform time interval between detection pulse periods. This can result in inaccurate measurements in situations where large background tissue motion occurs, such as, when examining the heart. Thus, to enable more accurate measurements, the PRF is increased during the detection pulse period. However, this results in non-uniform temporal sampling illustrated in the pulse timing sequence shown in FIG. 1B.

Figure 1B:
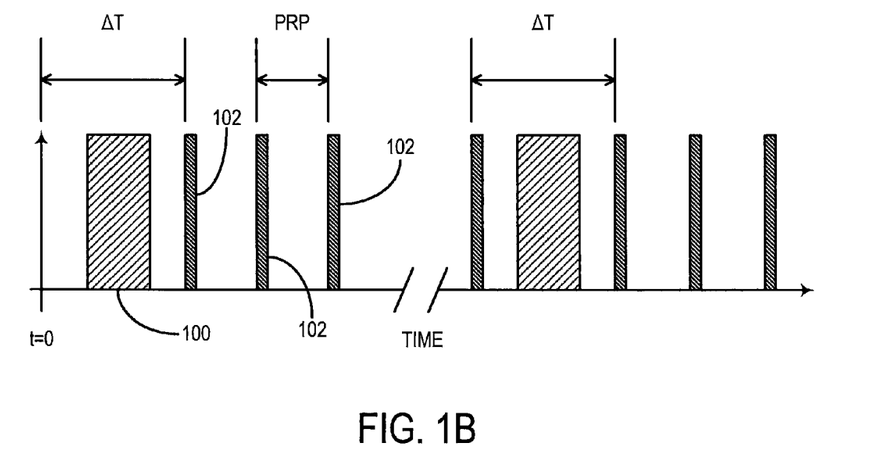
FIG. 1B is a pulse timing diagram indicating the application of ultrasonic vibration and detection pulses in a non-uniform pattern.

Referring particularly now to FIG. 1B, the ultrasonic vibration pulse 100, or pushing pulse, is applied during a time period of duration $\Delta T$. When the PRF of the ultrasonic detection pulses 102 is increased, the pulse repetition period ("PRP") is correspondingly decreased. Thus, a non-uniform temporal sampling is generally defined for those situations when $\Delta T > PRP$, as illustrated in FIG. 1B. On the other hand, a non-uniform temporal sampling also exists when $\Delta T < PRP$; however, this will result in aliasing and is a generally undesirable configuration. It is noted that the pulse timing sequence shown in FIG. 1A, where a uniform and lower PRF is employed, is very simple and may work well under certain conditions. In these situations where the duration of the pushing pulse period, $\Delta T$, is a multiple of the PRP, interpolation can be used on the vibration sequence demodulated from ultrasound echoes. As a result, the interpolated sequence will have uniform temporal sampling and, therefore, can be processed as if there are no missing data samples. While this approach works well for in vitro tissue experiments, the results will degrade if large background motion is present. Thus, this approach is likely limited for in vivo applications, which are likely to see large background motions. Also, as stated above, if the PRF is too low, the higher harmonics of the pushing pulses will exceed the Nyquist sampling limit of the motion detection ultrasound, which will result in aliasing artifacts.

The non-uniform temporal sampling approach shown in FIG. 1B provides a degree of flexibility in pulse sequence design. First, the pushing pulse 100 can be significantly longer than in uniform approaches, such as the one in FIG. 1A. A higher overall PRF can also be maintained, which provides some compensation when the signal-to-noise ratio ("SNR") is low for the detected signal indicative of the harmonic shear wave motion. As will now be described in detail, the non-uniform temporal sampling shown in FIG. 1B presents a processing challenge that is addresses during the Kalman filtering process.

Kalman filtering can be applied directly to non-uniform sampled data, if the measurement equation properly accommodates the differences between the pushing pulse period and the pulse repetition period ("PRP") of the detection pulses. Therefore, the state equation given by Eqn. (18) is applicable if modified, even when tissue motion is sampled non-uniformly in time. To achieve this, the measurement vector, $H_k$, is modified to properly account for the exact timing of each iteration, thereby providing a means by which the Kalman filter can accommodate non-uniform sampled sequence. With reference to the sampling pattern provided in FIG. 1B, the measurement vector, $H_k$, for the $k^{th}$ echo located between the $n^{th}$ and $(n+1)^{th}$ pushing pulse becomes:

$$H_k = [\sin(\omega_s(kT+n(\Delta T-T)))\cos(\omega_s(kT+n(\Delta T-T)))] \quad \text{Eqn. (23).}$$

Thus, when accounting for such a non-uniform temporal sampling, the Kalman filtering process is carried out using Eqns. (15), (17), (18), and (23). In this manner, uniform sampling is not required when the Kalman filter is appropriately modified to identify the next time step before each iteration.

In general, when performing SDUV the binary pushing pulses generate harmonics in addition to the fundamental pushing frequency, and these harmonics can introduce errors during the Kalman filtering process if they are not included in the vibration model utilized by the Kalman filter. This is because the Kalman filter assumes that the signal indicative of the harmonic motion contains only one frequency and that all other out-of-band motions are white noise. While this assumption is correct under certain circumstances, such as where one transducer is dedicated to maintain continuous monochromatic vibration within the studied tissue, it is not true when the binary pushing pulses contain a fundamental frequency (e.g., 100 Hz) and higher harmonics (e.g., 200 Hz, 300 Hz, and 400 Hz). Applying a band-pass filter centered on the frequency of interest to suppress other frequencies before the Kalman filtering is helpful, but a band-pass filter cannot remove all of the unwanted frequencies. Therefore, errors during the Kalman filtering process still exists. Moreover, digital band-pass filters assume a uniform sampling rate; therefore, this approach cannot be used directly on non-uniform sampled data.

Therefore, when non-uniform temporal sampling is employed, band-pass filtering no longer is applicable; however, the Kalman filter can be further modified to process multiple frequencies at the same time. The harmonics of the binary pushing pulses can be properly extracted by this multi-frequency Kalman filter, instead of being assumed as white noise. As a result, processing bias can be minimized.

As described above, and shown in Eqn. (17), two state variables are required to model one frequency. When adapting the Kalman filter to account for multiple frequencies, however, the number of state variables is increased to twice the number of frequencies that are to be estimated. That is, each frequency requires two state variables. For example, 10 state variables are required to model the fundamental frequency and its second, third, fourth, and fifth harmonics at the same time. In the multiple frequency adaptation, all the state variables are therefore optimized simultaneously in each iteration. With this multiple frequency approach, band-pass filtering is not required before applying the Kalman filter since all of the major signals are included in the Kalman filter formula; thus, there is no need to reject out-of-band colored signals.

For the multiple frequency Kalman filter modification, if there are N variation frequencies, or harmonics, to be estimated, the measurement vector, $H_k$, becomes:

$$H_k = [s_1 \, c_1 \, s_2 \, c_2 \ldots s_N \, c_N] \quad \text{Eqn. (24);}$$

where $s_m = \sin(m\omega_s kT)$, $c_m = \cos(m\omega_s kT)$, and $m = 1, 2, 3, \ldots, N$. For non-uniformly sampled data using, for example, the pulse timing sequence shown in FIG. 1B:

$$s_m = \sin(m\omega_s(kT+n(\Delta T-T))) \quad \text{Eqn. (25);}$$

and, $$c_m = \cos(m\omega_s(kT+n(\Delta T-T))) \quad \text{Eqn. (26).}$$

For N harmonics, the state variable vector, $x_k$, measurement vector, $H_k$, and the Kalman filter gain vector all have 2N elements. On the other hand, the transition matrix, $\Phi$, covariance matrix of the estimation errors, and the covariance matrix of the driving sequences all have a dimension of 2N×2N, which are extensions of the 2×2 matrices described above. While only the first few harmonics are generally useful when estimating the harmonic shear wave motion, all of the harmonics are included in the Kalman filtering process for more accurate estimations.

The first approach for compensating for large background tissue motion has been described in the foregoing paragraphs. However, as discussed above, another approach for compensating for the effects of gross tissue motion on the estimation of the phase and amplitude of the harmonic shear wave motion includes modeling these effects.

First, small background motions can be accommodated by the white driving sequence vector, $w_k$, in Eqn. (18), which allows limited variations in the vibration amplitude and phase over time. The variances of, $w_k$, are given by the $Q_k$ covariance matrix of the Kalman filter. When background motion is large, however, a random process can be used to model this motion, such as, for example, a random walk model. When incorporating this random walk model into the Kalman filtering process, two additional state variables are added to the state equation, Eqn. (18). One variable, $D_B(kT)$, is added to model the background displacement and another, $v_B(kT)$, to model the background velocity. Generally speaking, the velocity is driven by the white noise sequence, $w_k$, and the displacement is the integration of this velocity. Thus, these two additional state variables are added to the state variable vector, $x_k$, and the transition matrix, $\Phi$, is rewritten as:

$$\Phi = \begin{bmatrix} 1 & 0 & 0 & 0 \\ 0 & 1 & 0 & 0 \\ 0 & 0 & 1 & T \\ 0 & 0 & 0 & 1 \end{bmatrix}. \quad \text{Eqn. (27)}$$

Thus, Eqn. (18) is rewritten as:

$$x_k = \begin{bmatrix} 1 & 0 & 0 & 0 \\ 0 & 1 & 0 & 0 \\ 0 & 0 & 1 & T \\ 0 & 0 & 0 & 1 \end{bmatrix} x_{k-1} + w_k; \quad \text{Eqn. (28)}$$

where the state variable vector now has the form:

$$x_k = \begin{bmatrix} \beta\cos(\phi_s) \\ \beta\sin(\phi_s) \\ D_B(kT) \\ v_B(kT) \end{bmatrix}. \quad \text{Eqn. (29)}$$

As a result of this modification, the measurement vector, $H_k$, now becomes:

$$H_k=[\sin(\omega_s kT)\cos(\omega_s kT) 1\ 0] \quad \text{Eqn. (30);}$$

for uniform sampling, and for non-uniform sampling:

$$H_k=[\sin(\omega_s(kT+n(\Delta T-T)))\cos(\omega_s(kT+n(\Delta T-T))) 1\ 0] \quad \text{Eqn. (31).}$$

When multiple frequencies are simultaneously estimated, the state variables and the measurement vector are extended to include all frequencies in a similar way as shown in Eqns. (24)-(26).

The above method description is based on the tissue vibration displacement model using Eqn. (7). However, the same procedure is applicable to the tissue vibration velocity model when every sample in slow time is obtained from two consecutive I and Q data sets with the following change to Eqn. (7):

$$s(t_f, t_s) = -\tan^{-1}\left(\frac{Q(t_f, t_s)I(t_f, t_s + T) -}{Q(t_f, t_s + T)I(t_f, t_s)}\right) \quad \text{Eqn. (32)}$$
$$\frac{Q(t_f, t_s + T)I(t_f, t_s)}{I(t_f, t_s)I(t_f, t_s + T) +}$$
$$Q(t_f, t_s)Q(t_f, t_s + T)$$

Vibroacoustography System

Referring particularly again to FIG. 2, a vibroacoustography system which employs the present invention employs an ultrasonic transducer 311 that is operable to produce focused ultrasound beams. In particular, the transducer 311, such as a phased array transducer, intermittently transmits a beam of ultrasonic vibration pulses 100 to a vibration origin 200 in the tissue of interest 202 to vibrate, or oscillate, the tissue 202 at a prescribed frequency. When the vibration pulses are not being applied to the tissue 202, the focus of the transducer is electronically steered to a motion detection point 206 at a distance, $\Delta r$, from the vibration origin 200 and harmonic motion 204 at that point is detected. Under the direction of a digital controller of the ultrasound system 300, which controls the transmission and reception of signals, a vibration mode is multiplexed with a detection mode. This enables the detection of the harmonic motion 206 by the same transducer 311 as that transmitting the vibration pulses 100 and both vibration and detection can be achieved without mechanically moving the transducer 311.

Figure 3:
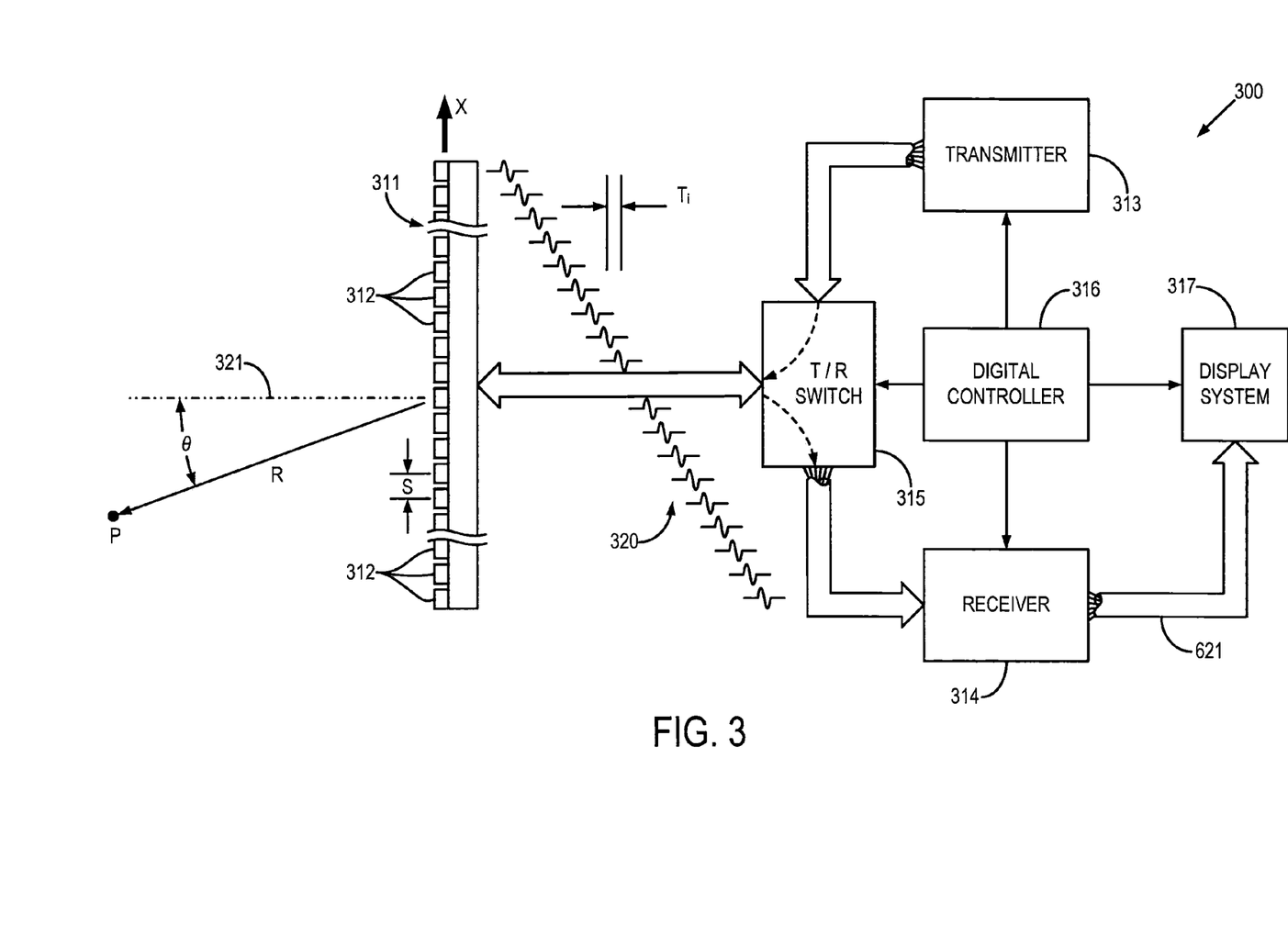
FIG. 3 is a block diagram of an ultrasound system used in the system of FIG. 2.

Referring particularly to FIG. 3, a transducer array 311 includes a plurality of separately driven elements 312 which each produce a burst of ultrasonic energy when energized by a pulse produced by a transmitter 313. The ultrasonic energy reflected back to the transducer array 311 from the subject under study is converted to an electrical signal by each transducer element 312 and applied separately to a receiver 314 through a set of switches 315. The transmitter 313, receiver 314, and the switches 315 are operated under the control of a digital controller 316 responsive to the commands input by the human operator. A complete scan is performed by acquiring a series of echoes in which the switches 315 are set to their transmit position, the transmitter 313 is gated on momentarily to energize each transducer element 312, the switches 315 are then set to their receive position, and the subsequent echo signals produced by each transducer element 312 are applied to the receiver 314. The separate echo signals from each transducer element 312 are combined in the receiver 314 to produce a single echo signal which is employed to produce a line in an image on a display system 317.

The transmitter drives the transducer array 311 such that the ultrasonic energy produced is directed, or steered, in a beam. A B-scan can therefore be performed by moving this beam through a set of angles from point-to-point rather than physically moving the transducer array 311. To accomplish this the transmitter 313 imparts a time delay, $T_i$, to the respective pulses 320 that are applied to successive transducer elements 312. If the time delay is zero $T_i=0$, all the transducer elements 312 are energized simultaneously and the resulting ultrasonic beam is directed along an axis 321 normal to the transducer face and originating from the center of the transducer array 311. As the time delay, $T_i$, is increased, the ultrasonic beam is directed downward from the central axis 321 by an angle, $\theta$.

A sector scan is performed by progressively changing the time delays $T_i$ in successive excitations. The angle $\theta$ is thus changed in increments to steer the transmitted beam in a succession of directions. When the direction of the beam is above the central axis 321, the timing of the pulses 320 is reversed.

Figure 4:
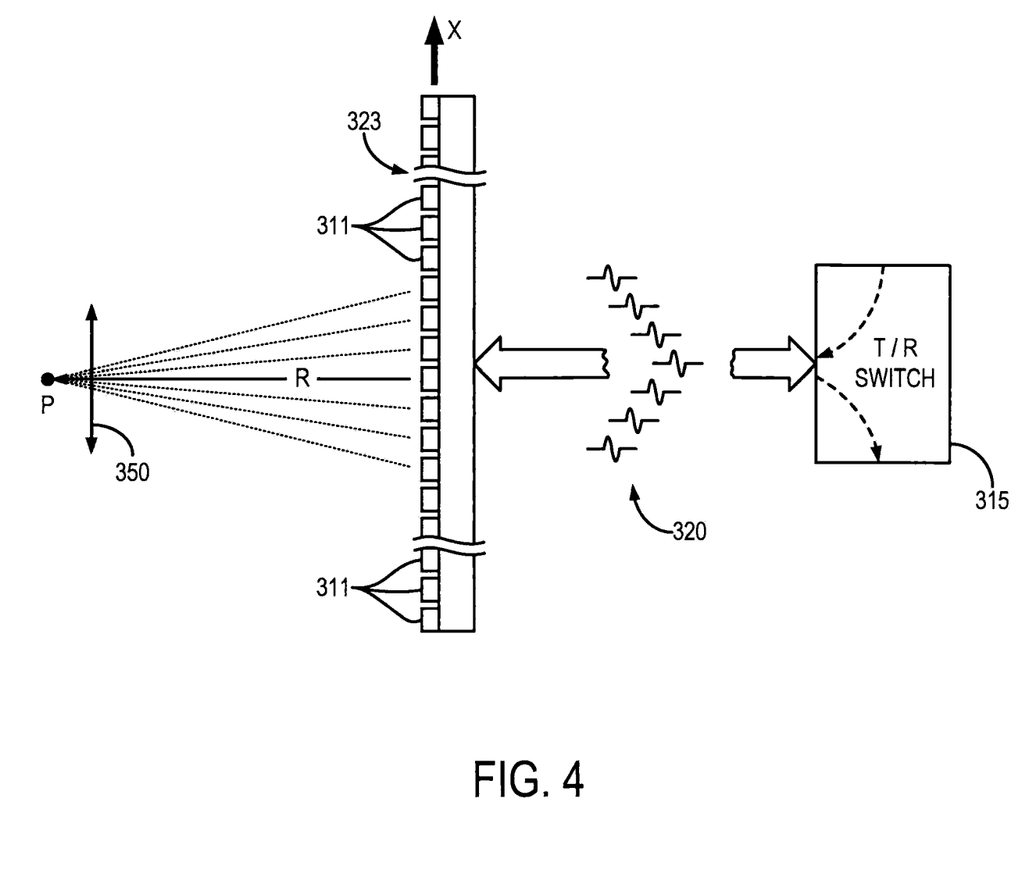
FIG. 4 is a block diagram of a linear ultrasound transducer that forms a part of one configuration of the ultrasound system of FIG. 3.

As shown in FIG. 4, a linear transducer array may also be employed in the ultrasonic imaging system of FIG. 3. In this embodiment the transmitter 313 drives the transducer array 311 such that an ultrasonic beam is produced which is directed substantially perpendicular to its front surface. Referring particularly to FIG. 4, to focus this beam at a range, R, from the transducer 311 a subgroup of the elements 312 are energized to produce the beam and the pulsing of the inner elements 312 in this subgroup are delayed relative to the outer elements 312 as shown at 320. A beam focused at point P results from the interference of the small separate wavelets produced by the subgroup elements. The time delays determine the depth of focus, or range R, and this is typically changed during a scan when a two-dimensional image is to be produced. The same time delay pattern is used when receiving the echo signals resulting in dynamic focusing of the echo signals received by the subgroup of elements 312. In this manner a single scan line in the image is formed.

To generate the next scan line, the subgroup of elements to be energized are shifted one element position along the transducer length and another scan line is required. As indicated by the arrow 350, the focal point, P, of the ultrasonic beam is thus shifted along the length of the transducer 311 by repeatedly shifting the location of the energized subgroup of elements 312.

Referring again particularly to FIG. 3, the echo signals produced by each burst of ultrasonic energy emanate from reflecting objects located at successive positions, R, along the ultrasonic beam. These are sensed separately by each segment 312 of the transducer array 311 and a sample of the magnitude of the echo signal at a particular point in time represents the amount of reflection occurring at a specific range, R. Due to the differences in the propagation paths between a focal point, P, and each transducer element 312, however, these echo signals will not occur simultaneously and their amplitudes will not be equal. The function of the receiver 314 is to amplify and demodulate these separate echo signals, impart the proper time delay to each and sum them together to provide a single echo signal which accurately indicates the total ultrasonic energy reflected from each focal point, P, located at range, R, along the ultrasonic beam oriented at the angle, $\theta$.

To simultaneously sum the electrical signals produced by the echoes from each transducer element 312, time delays are introduced into each separate transducer element channel of the receiver 314. In the case of the linear array 311, the delay introduced in each channel may be divided into two components, one component is referred to as a beam steering time delay, and the other component is referred to as a beam focusing time delay. The beam steering and beam focusing time delays for reception are precisely the same delays, $T_i$, as the transmission delays described above. However, the focusing time delay component introduced into each receiver channel is continuously changing during reception of the echo to provide dynamic focusing of the received beam at the range, R, from which the echo signal emanates.

Under the direction of the digital controller 316, the receiver 314 provides delays during the scan such that the steering of the receiver 314 tracks with the direction of the beam steered by the transmitter 311 and it samples the echo signals at a succession of ranges and provides the proper delays to dynamically focus at points, P, along the beam. Thus, each emission of an ultrasonic pulse results in the acquisition of a series of data points which represent the amount of reflected sound from a corresponding series of points, P, located along the ultrasonic beam.

By selecting proper time delays, echoes from multiple focused locations can be received to measure vibration information from several points of the tissue. The limitation of the lateral resolution of the transducer for two closely located points can be improved by assigning different transmitting codes for different locations.

The display system 317 receives the series of data points produced by the receiver 314 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive locations along the length of the transducer 311 (linear array mode) or steering angles (PASS mode) is performed to provide the data necessary for display of an image.

Figure 5:
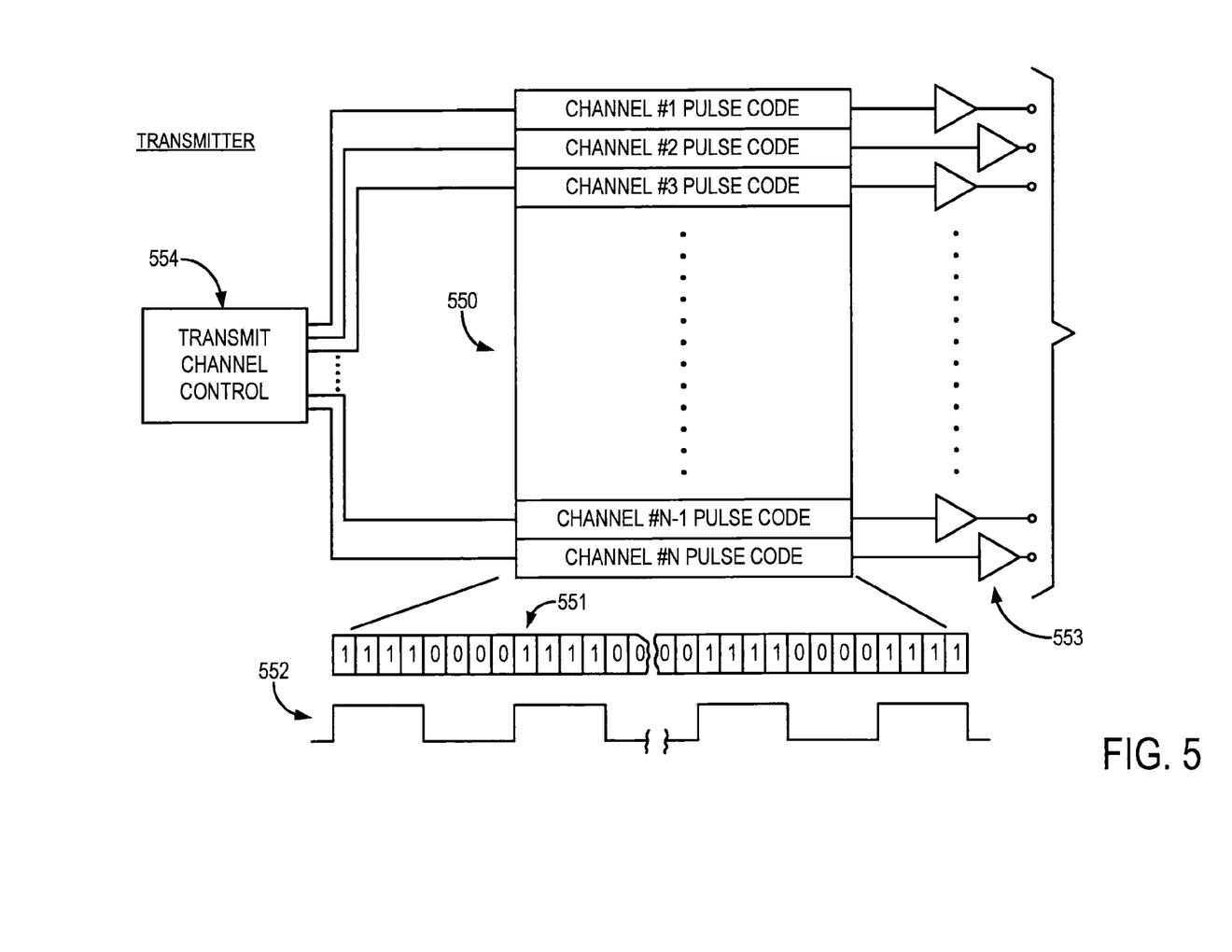
FIG. 5 is a block diagram of a transmitter which forms part of the ultrasound system of FIG. 3.

Referring particularly to FIG. 5, the transmitter 313 includes a set of channel pulse code memories which are indicated collectively at 550. Each pulse code memory 550 stores a bit pattern 551 that determines the frequency of the ultrasonic pulse 552 that is to be produced. This bit pattern is read out of each pulse code memory 550 by a master clock and applied to a driver 553 which amplifies the signal to a power level suitable for driving the transducer 311. In the example shown in FIG. 5, the bit pattern is a sequence of four "1" bits alternated with four "0" bits to produce a 5 megahertz ("MHz") ultrasonic pulse 552. The transducer elements 311 to which these ultrasonic pulses 552 are applied respond by producing ultrasonic energy.

As indicated above, to steer the transmitted beam of the ultrasonic energy in the desired manner, the pulses 552 for each of the N channels must be produced and delayed by the proper amount. These delays are provided by a transmit control 554 which receives control signals from the digital controller 316. When the control signal is received, the transmit control 554 gates a clock signal through to the first transmit channel 550. At each successive delay time interval thereafter, the clock signal is gated through to the next channel pulse code memory 550 until all the channels to be energized are producing their ultrasonic pulses 552. Each transmit channel 550 is reset after its entire bit pattern 551 has been transmitted and the transmitter 313 then waits for the next control signal from the digital controller 316.

Figure 6:
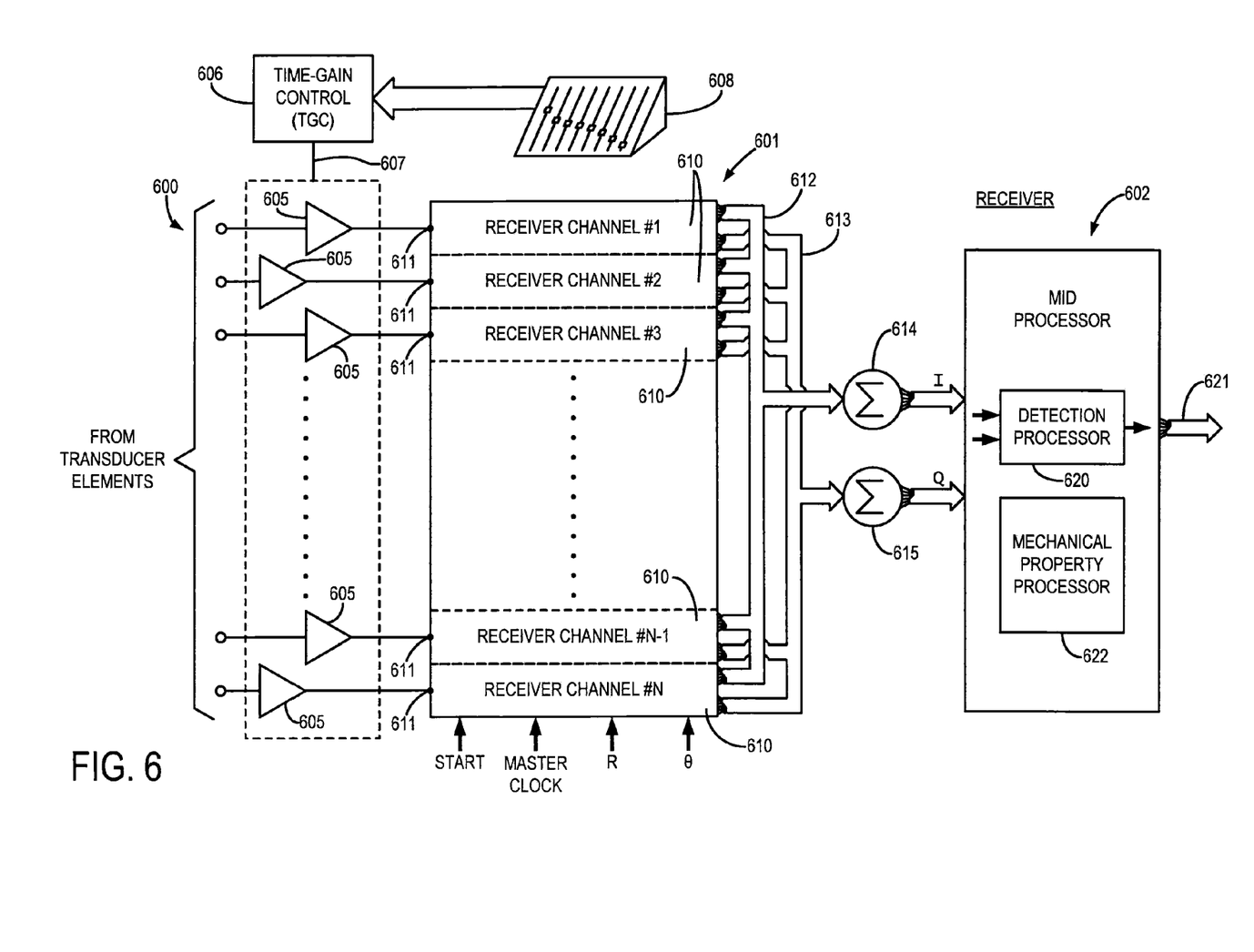
FIG. 6 is a block diagram of a receiver which forms part of the ultrasound system of FIG. 3.

Referring particularly to FIG. 6, the receiver 314 is comprised of three sections: a time-gain control ("TGC") section 600, a beam forming section 601, and a mid processor 602. The time-gain control section 600 includes an amplifier 605 for each of the N receiver channels and a time-gain control circuit 606. The input of each amplifier 605 is connected to a respective one of the transducer elements 312 to receive and amplify the echo signal which it receives. The amount of amplification provided by the amplifiers 605 is controlled through a control line 607 that is driven by the time-gain control circuit 606. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by the operator who manually sets TGC linear potentiometers 608 to values which provide a relatively uniform brightness over the entire range of the scan. The time interval over which the echo signal is acquired determines the range from which it emanates, and this time interval is divided into segments by the TGC control circuit 606. The settings of the potentiometers are employed to set the gain of the amplifiers 605 during each of the respective time intervals so that the echo signal is amplified in ever increasing amounts over the acquisition time interval.

The beam forming section 601 of the receiver 314 includes N separate receiver channels 610. Each receiver channel 610 receives the analog echo signal from one of the TGC amplifiers 605 at an input 611, and it produces a stream of digitized output values on an I bus 612 and a Q bus 613. Each of these I and Q values represents a sample of the echo signal envelope at a specific range, R. These samples have been delayed in the manner described above such that when they are summed at summing points 614 and 615 with the I and Q samples from each of the other receiver channels 610, they indicate the magnitude and phase of the echo signal reflected from a point, P, located at range, R, on the ultrasonic beam.

Referring still to FIG. 6, the mid processor section 602 receives the beam samples from the summing points 614 and 615. The I and Q values of each beam sample is a digital number which represents the in-phase and quadrature components of the magnitude of the reflected sound from a point, P. The mid processor 602 can perform a variety of calculations on these beam samples, where choice is determined by the type of image to be reconstructed. For example, if a conventional magnitude image is to be produced, a detection process indicated at 620 is implemented in which a digital magnitude, M, is calculated from each beam sample according to:

$$M=\sqrt{I^2+Q^2} \qquad \text{Eqn. (33).}$$

The resulting magnitude values output at 621 to the display system 317 result in an image in which the magnitude of the reflected echo at each image pixel is indicated by pixel brightness.

The present invention is implemented by a mechanical property processor 622 which forms part of the mid-processor 602. As will be explained in detail below, this processor 602 receives the I and Q beam samples acquired during a sequence of measurements of the subject tissue 202 and calculates a mechanical property of the tissue 202.

Shearwave Dispersion Ultrasound Vibrometry

Figure 7:
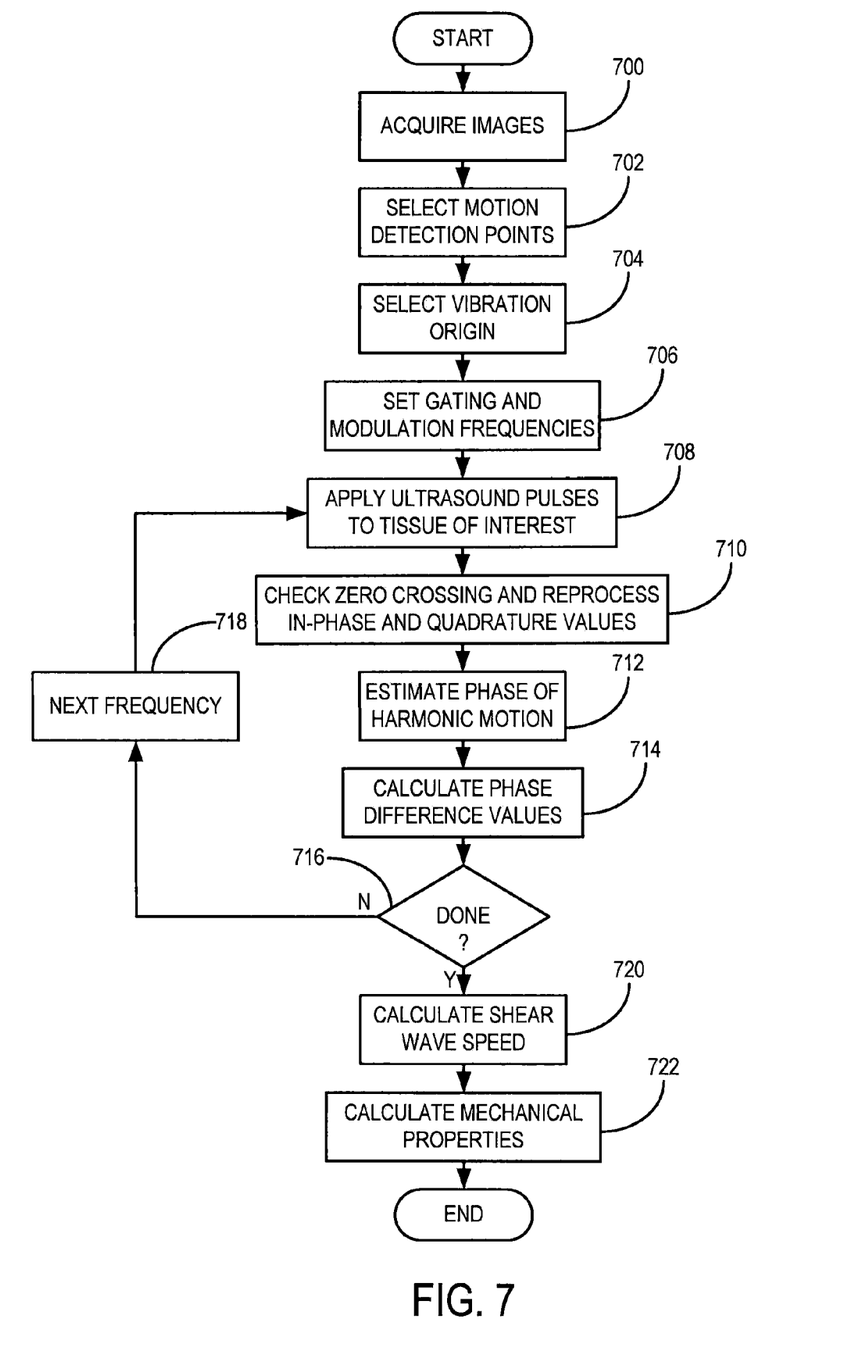
FIG. 7 is a flow chart setting forth the steps of a method for measuring the mechanical properties of a tissue of interest in accordance with the present invention.

Referring particularly to FIG. 7, a method for measuring mechanical properties, such as shear elasticity and shear viscosity, of a tissue of interest using a shear wave speed dispersion technique is performed with an ultrasound system 300, such as the one described above. The mechanical property processor 622 controls the measurements made by the ultrasound system 300, the vibration pulse output of the transducer elements 312, processes the resulting echo signals I and Q to satisfy the above-described Eqns. (5) and (6), and calculates a mechanical property of the target tissues. Such target tissues may be, for example, an artery or myocardial tissue, and the mechanical property may be stiffness.

The ultrasound system 300 is operated first using B-mode scanning to acquire an anatomical ultrasound image of a region of interest, such as the heart or liver, as indicated at step 700. Next, a target of interest is determined such as by selected in the ultrasound image a plurality of motion detection points at which it is desired to obtain mechanical properties, as indicated at step 702. Then, at process block 704, a vibration origin is selected. The vibration origin and the plurality of motion detection points are, for example, selected to be co-linear and spaced as discussed below. These selections can be provided to the ultrasound system in a variety of ways, such as, for example, by entering data, using a display to select among options, or using a touch screen or selector on an ultrasound image screen.

As previously described herein, the shear wave speed dispersion technique makes use of an estimation of wave speed using equation (22), which includes a phase difference, such that the phase $\phi_s$, of the echo signals is determined at a plurality of points. This is achieved, for example, using a single vibration origin and two different motion detection points each located a different distance from the vibration origin; however, it is also possible to use a single detection point and change the vibration origin.

The determination of a desired distance, R, between a vibration origin and a motion detection point and the determination of a desired spacing, $\Delta r$, between the motion detection points can be based on a consideration of the type of tissue that is under examination. For example, an appropriate distance, R, in the liver may be on the order of one centimeter, while an appropriate distance, R, for a breast lesion may be on the order of five millimeters. The outgoing shear wave generated at the vibration origin using amplitude modulated pulses can be approximated as a cylindrical shear wave. Its amplitude decreases as the wave propagates outwards from the excitation center due to both geometry effects and attenuation resulting from the medium in which the wave propagates. Therefore, it is desirable to have the detection points close to the vibration origin to get higher vibration amplitude. On the other hand, locations too close to the vibration origin will be subject to the near field effect and thus the phase of the shear wave will deviate from a linear relationship with the traveled distance. This near field effect increases for stiffer tissue. However, $\Delta r$ can not be too large, otherwise the vibration amplitude will be too small for reliable phase estimation. Therefore, the precision of shear wave dispersion characterization can be improved by optimizing the position and range of vibration detections, which may be dependent on the type of tissue under evaluation, and by increasing the vibration amplitude as discussed above.

Referring particularly again to FIG. 7, after the vibration origin and motion detection points have been selected, the gating frequency and the modulation frequency of the ultrasonic pulses are determined, as indicated at step 706. For example, in one embodiment, the gating frequency is 2.5 kHz and a prescribed modulation frequency for a first shear wave speed is 100 Hz. Next, the transmission of intermittent ultrasonic vibration pulses to a vibration origin, and the transmission of ultrasonic detection pulses and the receipt of echo signals from the motion detection point occurs under the control of the digital controller 316 of the ultrasound system 300, as indicated at step 708. The ultrasonic vibration pulses are amplitude modulated ("AM") and are applied to the subject in an on-off time sequence with a detection mode occurring during the off intervals of the vibration pulses.

By way of example, the non-uniform temporal pulse sequencing illustrated in FIG. 1B is employed, wherein the duration of the "on" period when the pushing pulse 100 is applied, $\Delta T$, is larger than the pulse repetition period ("PRP") of the ultrasonic detection pulses 102. The "on" phase of this sequence essentially comprises an intermittent or gated AM signal composed of ultrasonic vibration pulses that are modulated at a modulation frequency. The application of a continuous wave AM signal to a subject in this manner generates a radiation force having a frequency equal to the modulation frequency of the beam. In turn, the radiation force imparts a harmonic shear wave 204 to the tissue if interest 202. Similarly, the application of a gated rather than a continuous AM signal generates a radiation force including various frequency components and a shear wave 204 including these frequency components is imparted to the subject tissue 202.

It should be apparent that two focused ultrasound beams having a beat frequency can also be employed for vibrating the tissue 202. The two beams can be achieved by dividing the elements 312 of the transducer array 311 into two groups and using the first group to transmit ultrasonic pulses at a first frequency, $\omega_1$, and the second group to transmit ultrasonic pulses at a second frequency, $\omega_2$. For example, the first frequency may be 1 MHz+100 Hz and the second frequency may be 1 MHz−100 Hz. Such a dual beam will vibrate the tissue 202 at the difference frequency, which in this example is 200 Hz. The same concept of intermittent vibration and detection can be used to measure a characteristic of an imparted shear wave in order to characterize a mechanical property of a subject.

Referring still to FIG. 7, the ultrasound system 300 is operated to acquire echo signals from the subject tissues at a series of motion detection points. By way of example, when measuring the mechanical properties of an artery 100 echoes sampled at a 40 MHz sample rate are acquired at each of 11 motion detection points that are spread evenly along 10 to 20 mm of the length of the artery are measured. Eight echo samples at the desired location are used to obtain average I and Q values.

The ultrasonic detection pulses can be applied to the motion detection points in a number of ways. For example, each motion detection point can be fully sampled before the detection pulses are steered to the next point. However, in the alternative the plurality of motion detection points can be sampled substantially contemporaneously. In one configuration, parallel beamforming is employed it both the transmission of the detection pulses and the reception of the resulting echo signals. In general, a substantially plane wave is produced in the region of the tissue of interest undergoing harmonic shear wave motion by properly phasing the transducer elements 312. This results in a rather broad beam instead of a focused ultrasound beam. The backscattered ultrasound is then formed into focused beams in a beamformer after being received by the transducer 311. In another configuration, the transducer elements 312 are energized in subgroups such that a plurality of focused ultrasound beams are directed to the plurality of motion detection points.

In yet another configuration, the motion detection points can be sampled in a so-called interleaved manner. In this configuration, an ultrasonic detection pulse is applied to the $j^{th}$ motion detection point either before or after an echo is received from the $(j-1)^{th}$ motion detection point. The time difference between the transmission of an ultrasonic detection pulse to the $(j-1)^{th}$ and $j^{th}$ detection point is thereby defined as $T_d$. In this manner, the echo signal received from the $j^{th}$ motion detection point has the form:

$$y_k(kT_s,z_j)=\beta \sin(\omega_s kT_s+\omega_s(j-1)T_d+\phi_s(z_j)) \quad \text{Eqn. (34)};$$

where j=1, 2, 3, . . . , M, and M is the number of motion detection points; k=1, 2, 3, . . . , N, and N is the number of samples at each motion detection point in slow time (i.e., the number of ultrasonic detection pulses applied to each point); $T_s=MT_d$ is the duration of time between the transmission of ultrasonic detection pulses to the same motion detection point; $z_j$ is the location of the $j^{th}$ motion detection point; and $\phi_s(z_j)$ is the phase of the harmonic shear wave motion at the $j^{th}$ motion detection point. This interleaved sampling pattern can be readily employed using a phased array transducer with proper beamforming, as is known in the art. By acquiring the received echo signals in this manner, they are samples of the harmonic shear wave motion at different times; thus, a phase estimate (for example, as estimated by Kalman filtering) of the harmonic shear wave motion needs to be corrected accordingly. Given the received echo signals, the phase estimated by the Kalman filter for the $j^{th}$ motion detection point is:

$$\tilde{\phi}_s(z_j)=\omega_s(j-1)T_d+\phi_s(z_j) \quad \text{Eqn. (35)}.$$

Thus, the phase of the harmonic shear wave motion at the $j^{th}$ motion detection point, $\phi_s(z_j)$, should be corrected as:

$$\phi_s(z_j)=\tilde{\phi}_s(z_j)-\omega_s(j-1)T_d \quad \text{Eqn. (36)}.$$

Referring again to FIG. 7, and as described above, it is necessary that all the I values remain either positive or negative in order to properly detect the signal indicative of the harmonic shear wave motion when the displacement model of Eqn. (7) is utilized; however, when the velocity model of Eqn. (32) is utilized, this is not necessary. As indicated at process block 710, the I values are checked and if a zero crossing occurs, all the I and Q values are reprocessed to add a constant phase, $\phi_0$, as indicated above in equations (5) and (6). Such a constant phase is added until no zero crossings are detected.

As indicated at process block 712, the amplitude and phase of the tissue motion at each point is then estimated from the acquired I and Q echo samples. As described above there are a number of different methods for accomplishing this, but the arctangent of the ratio of the Q and I beam samples are calculated and the mean value is removed to obtain the harmonic motion in slow time, as indicated above in Equations (7) and (8). The harmonic motion is modeled by a second order differential equation with random amplitude and phase and the known beat frequency. The amplitude and phase is then estimated in a recursive, Kalman filter process that minimizes the mean square error between the model and the measured tissue harmonic motion given by:

$$P_k=E[(x_k-\hat{x}_k)(x_k-\hat{x}_k)^T] \quad \text{Eqn. (37)};$$

where $\hat{x}_k$ is an estimate for the state variable vector, $x_k$. When the non-uniform temporal sampling shown in FIG. 1B is employed, the Kalman filtering is performed using Eqns. (15), (20), and (21). Here, the state variable vector, $x_k$, is given by the state equation of Eqn. (28):

$$x_k = \begin{bmatrix} 1 & 0 & 0 & 0 \\ 0 & 1 & 0 & 0 \\ 0 & 0 & 1 & T \\ 0 & 0 & 0 & 1 \end{bmatrix} x_{k-1} + w_k;$$

and the measurement vector, $H_k$, employed is that of Eqn. (31):

$$H_k=[\sin(\omega_s(kT+n(\Delta T-T)))\cos(\omega_s(kT+n(\Delta T-T)))1\ 0].$$

As discussed above, by performing the Kalman filtering in this manner, not only is the non-uniform temporal sampling accounted for, but large background tissue motions are compensated for using an integrated random walk model. It should be appreciated by those skilled in the art, however, that the state equation employed need not include this random walk model in every situation. In applications such as those, the state equation and measurement matrix employed would be those of Eqns. (18) and (23), respectively. Moreover, when it is desirable to estimate a plurality of shear wave frequencies at one time, the measurement vector, $H_k$, is modified in accordance with Eqns. (24)-(26).

As indicated by process block 714, the change in tissue oscillation phase as a function of distance is then calculated for this beat frequency using the calculated phase values at the 11 points along the artery. As indicated by process block 716, the digital controller determines whether the last frequency has been measured. If not, at process block 718, another frequency is selected and process blocks 708-714 are repeated at each desired prescribed frequency. For example, shear wave speeds are calculated using a set of modulation frequencies including 100 Hz, 200 Hz, 300 Hz, 400 Hz and 500 Hz.

As indicated at process block 720, the next step is to calculate the shear wave speeds in the subject tissue 202 at the different beat frequencies. Linear regression is applied to the 11 phase changed measurements to yield a phase change over 10 mm distance along the artery. From this phase change over distance information, the shear wave speed at each beat frequency is estimated as described with reference to equation (22).

As indicated at process block 722, the final step is to calculate a mechanical property of the tissue 202 from the shear wave speed information. In the preferred embodiment the shear elasticity and viscosity of the tissue 202 is estimated from the set of shear wave speeds. These mechanical properties indicate the stiffness of the artery, which is a valuable clinical measurement, but also, for example, the stiffness of myocardial and liver tissue. This calculation is based on shear wave speed dispersion as described, for example, by S. Chen, et al., in "Complex Stiffness Quantification Using Ultrasound Stimulated Vibrometry," *IEEE Ultrasonics Symposium*, 2003; 941-944. The shear wave speeds at multiple frequencies are fit with appropriate theoretical models to solve for the shear elasticity and viscosity. For example, one appropriate equation is the so-called Voigt model:

$$c_s = \sqrt{\frac{2(\mu_1^2 + \omega^2\mu_2^2)}{\rho(\mu_1 + \sqrt{\mu_1^2 + \omega^2\mu_2^2})}}\ ; \quad \text{Eqn. (38)}$$

where $c_s$ is the shear wave speed, $\mu_1$ is the shear modulus, $\mu_2$ is the shear viscosity, $\omega$ is frequency, and $\rho$ is the density of the tissue, which can be assumed to be 1000 kilograms per cubic meter (kg/m$^3$).

While the analysis of the received echo signal is performed in the mid-processor section of an ultrasound receiver in the preferred embodiment described above, it should be apparent that these functions can also be performed in a separate processor or computer workstation.

Thus, in general, harmonic motion is detected at a motion detection point by transmitting detection pulses to the motion detection point and receiving echo pulses therefrom. These signals are then analyzed as described above in the mid-processor 602 of the receiver 314. A signal indicative of the induced harmonic shear wave motion is detected at the prescribed frequency in the received ultrasonic echo signals and a characteristic of the detected signal, such as amplitude and/or phase, is determined. The mechanical property is then calculated using the measured characteristic. Depending on the model used to relate a measured characteristic to a mechanical property, it may be necessary to determine a measured characteristic at more than one point and/or at more than one frequency. For example, using the Voigt model requires shear wave speed to be calculated at a plurality of prescribed frequencies. Using equation (22) to calculate the shear wave speed, $c_s$, requires phase measurements at two or more motion detection points.

In other embodiments, rather than measuring a phase difference and using the Voigt model, an amplitude could be measured and the change in amplitude over distance could be determined and used in conjunction with an appropriate model to determine one or more other mechanical properties of the subject target tissue.

Another way to vibrate tissue at one or more prescribed frequencies is by using tone bursts of ultrasonic pulses. The tone bursts are not modulated but have a specific amplitude, duration and period such that they impart a force having desired frequency components. For example, using tone bursts of ultrasonic pulses having a duration of 1 ms and repeated every 10 ms will generate a radiation force that includes frequency components at a fundamental frequency and multiples thereof, for example at 100 Hz, 200 Hz, 300 Hz, 400 Hz and 500 Hz. Using such a waveform for vibration provides advantages in faster data acquisition as described below as well as in lower tissue and transducer heating. When implementing this method for vibrating the target tissue, the measurements need not be repeated over different frequencies, since the tone bursts include frequency components at multiple frequencies. These tone bursts are also easier to implement using a conventional ultrasound system and the average intensity and power would be lower as compared to for example a similar gated AM modulation method. Further, because the off interval is generally longer when utilizing tone bursts, the detection pulses can be steered to more than one motion detection point during the off intervals.

Other embodiments of the invention are also possible. For example, an ultrasound system can be used for excitation in a manner such as described herein, and other known means, such as MRI or optical methods, can be used to detect the ultrasound motion.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for measuring a mechanical property of a subject, the steps comprising:
    a) applying, with an ultrasonic transducer and during a time period having a duration $\Delta T$, an ultrasonic vibration pulse to a vibration origin in a subject in order to impart harmonic motion at a prescribed frequency to the subject;
    b) applying, with the ultrasonic transducer and following the time period, a plurality of ultrasonic detection pulses to a motion detection point in the subject with a pulse repetition period (PRP) smaller than $\Delta T$, thereby resulting in non-uniform temporal sampling of the harmonic motion;
    c) receiving, with the ultrasonic transducer, echo signals from the motion detection point;
    d) detecting, in the received echo signals, a signal indicative of the harmonic motion at the prescribed frequency;
    e) determining at least one of a phase and an amplitude of the detected signal; and
    f) calculating a mechanical property of the subject using the measured at least one of a phase and an amplitude of the detected signal.

2. The method as recited in claim 1 in which step d) includes filtering the received echo signals.

3. The method as recited in claim 2 in which filtering the received echo signals in step d) is performed using a Kalman filter.

4. The method as recited in claim 3 in which the Kalman filter employed in step d) accounts for non-uniform temporal sampling of the received echo signals.

5. The method as recited in claim 4 in which steps a)-c) are repeated and during each repetition the ultrasonic detection pulses are applied to a different motion detection point.

6. The method as recited in claim 4 in which the Kalman filter employed in step d) further compensates for errors arising from gross tissue motion by employing an integrated random walk model.

7. The method as recited in claim 3 in which the Kalman filter employed in step d) accounts for a fundamental frequency and higher harmonic frequencies of the harmonic motion.

8. The method as recited in claim 3 in which the Kalman filter employed in step d) includes a model that compensates for errors arising from gross tissue motion.

9. The method as recited in claim 8 in which the model is an integrated random walk model.

10. The method as recited in claim 1 in which step b) includes applying the ultrasonic detection pulses to a plurality of motion detection points.

11. The method as recited in claim 10 in which step b) includes applying the ultrasonic detection pulses to the plurality of motion detection points substantially contemporaneously.

12. The method as recited in claim 10 in which step b) includes applying the ultrasonic detection pulses to the plurality of motion detection points in an interleaved manner.

13. The method as recited in claim 12 in which step e) includes correcting the measured phase of the signal for phase shifts arising from the interleaved manner in which the plurality of motion detection points are sampled.

14. An ultrasound system for practicing shearwave dispersion ultrasound vibrometry comprising:
    an ultrasound transducer for applying ultrasound to a subject;
    a controller for directing the ultrasound transducer to:
        apply, during a time period having a duration $\Delta T$, an ultrasonic vibration pulse to a vibration origin in the subject in order to impart harmonic motion at a prescribed frequency to the subject;
        apply, with the ultrasonic transducer and following the time period, a plurality of ultrasonic detection pulses to a motion detection point in the subject with a pulse repetition period (PRP) smaller than $\Delta T$, thereby resulting in non-uniform temporal sampling of the harmonic motion; and
        receive echo signals from the motion detection point; and a processor configured to:
- detect, in the received echo signals, a signal indicative of the harmonic motion at the prescribed frequency;
- determine a characteristic of the detected signal; and
- calculate a mechanical property of the subject using the measured characteristic of the detected signal.

15. The system as recited in claim 14 in which the processor is further configured to filter the received echo signals with a Kalman filter that accounts for non-uniform temporal sampling of the received echo signals.

* * * * *